US012589373B2

(12) United States Patent
Venkatakrishnan et al.

(10) Patent No.: US 12,589,373 B2
(45) Date of Patent: Mar. 31, 2026

(54) ULTRASHORT LASER SYNTHESIS OF NANOPARTICLES OF ISOTOPES

(71) Applicants: Krishnan Venkatakrishnan, Toronto (CA); Bo Tan, Toronto (CA)

(72) Inventors: Krishnan Venkatakrishnan, Toronto (CA); Bo Tan, Toronto (CA)

(73) Assignees: Krishnan Venkatakrishnan, Toronto (CA); Bo Tan, Toronto (CA)

( * ) Notice: Subject to any disclaimer, the term of this patent is extended or adjusted under 35 U.S.C. 154(b) by 547 days.

(21) Appl. No.: 18/018,406

(22) PCT Filed: Jul. 29, 2021

(86) PCT No.: PCT/CA2021/051064

§ 371 (c)(1),
(2) Date: Jan. 27, 2023

(87) PCT Pub. No.: WO2022/020959

PCT Pub. Date: Feb. 3, 2022

(65) Prior Publication Data

US 2023/0285916 A1     Sep. 14, 2023

Related U.S. Application Data

(60) Provisional application No. 63/059,079, filed on Jul. 30, 2020.

(51) Int. Cl.
B01J 2/00 (2006.01)
G01N 21/64 (2006.01)
(Continued)

(52) U.S. Cl.
CPC ............ B01J 2/00 (2013.01); G01N 21/6428 (2013.01); G01N 21/658 (2013.01);
(Continued)

(58) Field of Classification Search
CPC ..... B01J 2/00; G01N 21/658; G01N 21/6428; G01N 33/533; H05H 1/24
See application file for complete search history.

(56) References Cited

U.S. PATENT DOCUMENTS 6,586,696 B1 * 7/2003 Pronko .................. B01D 59/44
                                                          204/157.22
8,126,104 B2 * 2/2012 Schenter ................ G21G 1/001
                                                            376/196
(Continued)

OTHER PUBLICATIONS

International Search Report and Written Opinion mailed Sep. 27, 2021, in related International Application No. PCT/CA2021/051064.

*Primary Examiner* — Abdulmajeed Aziz
*Assistant Examiner* — Nathaniel J Lee
(74) *Attorney, Agent, or Firm* — Smart & Biggar LP

(57) ABSTRACT

Methods of synthesizing nanoparticles of an isotope using a laser beam are described herein. The methods include generating the laser beam, directing the laser beam to the target to convert the target into a plasma state, and bombarding the target in the plasma state with the laser beam to maintain the target in the plasma state and synthesize the nanoparticles of the isotope. During bombarding the target in the plasma state with the laser beam, the laser beam is configured to have a pulse frequency and peak laser intensity that accelerates electrons in the plasma state and maintains the plasma state at a temperature high enough to provide for the synthesis of the nanoparticles of the isotope. Apparatuses for synthesizing nanoparticles of an isotope using a laser beam are also described herein.

20 Claims, 6 Drawing Sheets

Free-particle nano-isotope synthesis

(51) Int. Cl.
   G01N 21/65      (2006.01)
   G01N 33/533      (2006.01)
   H05H 1/24      (2006.01)
   *B82Y 15/00*      (2011.01)
   *B82Y 20/00*      (2011.01)
   *B82Y 40/00*      (2011.01)

(52) U.S. Cl.
   CPC ............. G01N 33/533 (2013.01); H05H 1/24
       (2013.01); *B82Y 15/00* (2013.01); *B82Y 20/00*
       (2013.01); *B82Y 40/00* (2013.01); *G01N*
       *2021/6439* (2013.01)

(56)                References Cited

U.S. PATENT DOCUMENTS

| | | | |
|---|---|---|---|
| 2002/0106046 A1* | 8/2002 | Fujimoto | ................. G21G 1/12 |
| | | | 376/156 |
| 2002/0106064 A1 | 8/2002 | Fujimoto et al. | |
| 2016/0172065 A1* | 6/2016 | Labaune | ................. G21G 1/10 |
| | | | 376/190 |

* cited by examiner

100

102

Converting a target to a plasma state

104

Bombarding the target with the laser beam to synthesize nanoparticles of the isotope Laser pulses nanoisotopes nucleus plume Direct writing system for nano-isotope synthesis waveplate

600

606

604

602

608 mirror

Beam
Expander or
Harmonic
generator

Ultrashort
laser

610 focusing lens

Gas
nozzle
612 plasma plume 620 rpm vaccum collector 624 isotope soot 622 rotor 619 target material 618 quartz tube 614

Free-particle nano-isotope synthesis

ULTRASHORT LASER SYNTHESIS OF NANOPARTICLES OF ISOTOPES

CROSS-REFERENCE TO RELATED APPLICATION

This application is a 35 USC 371 national stage entry of PCT/CA2021/051064 filed on Jul. 29, 2021, and which claims the benefit of U.S. Provisional Patent Application No. 63/059,079 filed Jul. 30, 2020. The entire contents of each of these documents are hereby incorporated herein in its their entirety.

FIELD

This disclosure relates generally to creating isotopes, and more specifically to creating nanoparticles of an isotope using a laser.

BACKGROUND

Stable non-radioactive isotopes are used as labels to integrate, indicate, record and trace fundamental processes. For instance, in medical research and medical applications, stable isotopes can be used as tracers to investigate human metabolism, including but not limited to cancer metabolism.

Currently there are two major approaches in stable isotope enrichment: electromagnetic and gas centrifuge isotope separation technologies. Both of these methods do not synthesize stable isotopes, but rather isolate naturally occurring stable isotopes from minerals. Accordingly, these processes do not involve physio-chemical reactions and require large equipment to provide for the production of quantities of stable isotopes in volumes measured in the range of milligrams to kilograms.

Radioactive isotopes have many applications, particularly in medical fields where they are used for diagnosis and therapy. Currently, radioactive isotopes are typically isotopes of heavier elements and only rarely are isotopes of light elements.

Further, nanoparticles (i.e. particles less than 100 nm in size) of stable isotopes from light elements offer increased sensitivities in medical research and medical applications as tracers when compared to the products of the enrichment processes noted above, which are typically a powder of fine particles having diameters in a range of millimeter or submillimeter (e.g. micrometer) sizes.

Currently, there is no technique available to synthesis isotopes from light elements and there is no technique capable of producing nanoparticles of isotopes. Accordingly, there is a need for improved methods and systems of synthesizing stable isotopes from light elements and, more specifically synthesizing nanoparticles of isotopes from light elements, including oxygen (O), nitrogen (N), carbon (C), silicon (Si), and commonly used metals (such as but not limited to copper (Cu), iron (Fe), titanium (Ti), aluminum (Al), nickel (Ni), and the like.

SUMMARY

In accordance with a broad aspect, a method of synthesizing nanoparticles of an isotope from a target using a laser beam is described herein. The method includes generating the laser beam, directing the laser beam to the target to convert the target into a plasma state and bombarding the target in the plasma state with the laser beam to maintain the target in the plasma state and synthesize the nanoparticles of the isotope. During bombarding the target in the plasma state with the laser beam, the laser beam is configured to have a pulse frequency and a peak laser intensity that accelerates electrons in the plasma state and maintains the plasma state at a temperature high enough to provide for the synthesis of the nanoparticles of the isotope.

In at least one embodiment, during bombarding the target in the plasma state, the laser beam has a laser pulse width duration in a range of about 1 femtosecond (fs) to about 300 picoseconds (ps).

In at least one embodiment, during bombarding the target in the plasma state, the laser beam has a laser pulse width duration in a range of about 10 fs to about 10 ps.

In at least one embodiment, during bombarding the target in the plasma state, the laser beam has an average laser power that is greater than about 8 watts.

In at least one embodiment, during bombarding the target in the plasma state, the laser beam has an average laser power in a range of about 10 watts to about 100 watts.

In at least one embodiment, during bombarding the target in the plasma state, the laser has a pulse frequency in a range of about 200 kHz to about 250 MHz.

In at least one embodiment, during bombarding the target in the plasma state, the laser has a pulse frequency in a range of about 1 MHz to about 100 MHz.

In at least one embodiment, during bombarding the target in the plasma state, the laser has a laser wavelength in a range of about 250 nm to about 1150 nm at fundamental or higher harmonic frequency.

In at least one embodiment, during bombarding the target in the plasma state, the laser has a laser wavelength in a range of about 345 nm to about 1064 nm at fundamental or higher harmonic frequency.

In at least one embodiment, during bombarding the target in the plasma state, the laser has a focused laser spot size in a range of about 10 nm to about 2000 $\mu$m.

In at least one embodiment, during bombarding the target in the plasma state, the laser has a focused laser spot size in a range of about 5 nm to about 500 $\mu$m.

In at least one embodiment, during bombarding the target in the plasma state, the laser has a peak laser intensity that is greater than about $10^8$ W/cm$^2$.

In at least one embodiment, during bombarding the target in the plasma state, the laser has a peak laser intensity that is greater than about $10^{14}$ W/cm$^2$.

In at least one embodiment, during the bombarding the target in the plasma state, the laser has a peak laser intensity greater than about $10^{15}$ W/cm$^2$ and a pulse frequency of about 200 kHz.

In at least one embodiment, during the bombarding the target in the plasma state, the laser has a peak laser intensity greater than about $10^{14}$ W/cm$^2$ and a pulse frequency greater than about 1 MHz.

In at least one embodiment, the synthesized nanoparticle isotopes have a stable state or a half-life time greater than about 20 minutes.

In at least one embodiment, the nano isotopes are used for biological diagnostic applications to generate high fluorescence excitation signals.

In at least one embodiment, the nano isotopes are used for biological diagnostic applications to generate high surface enhanced Raman excitation signals.

In at least one embodiment, the nanoparticle isotopes are used in biomedical applications and have a biodegradable property.

In at least one embodiment, the nanoparticle isotopes are for use in biomedical applications and have a cellular self-metabolic property.

In at least one embodiment, the nanoparticle isotopes are for use in biomedical application and have a high cellular and tissue uptake efficiency.

In at least one embodiment, the nanoparticle isotopes are for use in biomedical applications and have a retention time in a biological cell in a range of about a one hour to about two months.

In accordance with another broad aspect, an apparatus for synthesizing nanoparticles of an isotope from a target using a laser beam is described herein. The apparatus includes a laser that is configured to generate laser beam pulses and an optical arrangement that is optically coupled to the laser source and configured to receive the laser beam pulses and direct the laser beam pulses towards the target. The laser beam pulses are generated at a pulse frequency and a peak laser intensity to convert the target into a plasma state, maintain the target material in the plasma state at a temperature high enough to synthesize the nanoparticles of the isotope.

In at least one embodiment, the apparatus includes a vacuum chamber housing the target, the vacuum chamber having an inlet for receiving a background gas and directing the background gas towards the target while the target is ablated by the laser beam pulses.

In at least one embodiment, the apparatus includes a tube housing the target, the tube having an inlet for receiving a gas and directing the gas towards the target while the target is ablated by the laser beam pulses to generate a plasma plume and an isotope soot.

In at least one embodiment, the apparatus includes a vacuum collector configured to collect the isotope soot.

In at least one embodiment, the apparatus includes a rotor configured to rotate the target within the tube as the target is ablated by the laser beam pulses.

In at least one embodiment, the apparatus includes a vessel housing the target, the vessel being filled with a liquid medium and the target being positioned within the vessel below a surface of the liquid medium.

In at least one embodiment, the liquid medium is a solvent.

In at least one embodiment, the solvent is one of distilled water, alcohol and an aqueous solution of polyvinylpyrrolidone.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figures 1, 2:
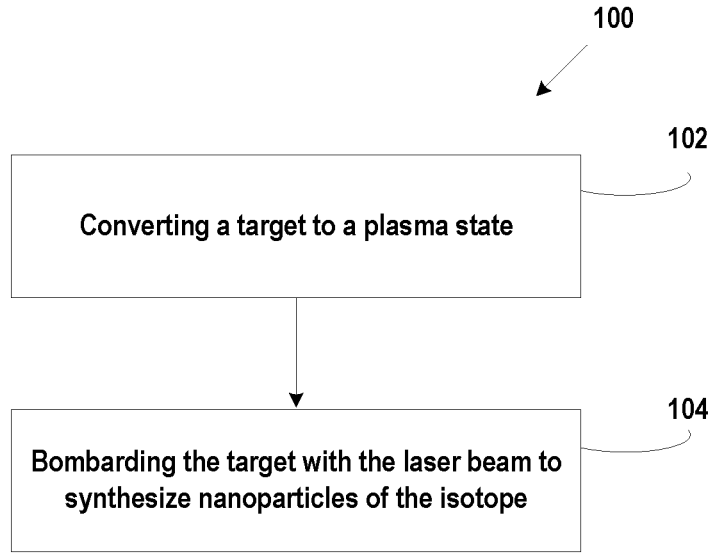
FIG. 1 shows a block diagram showing an example embodiment of a method for synthesizing nanoparticle isotopes from a target material in accordance with the teachings herein.
FIG. 2 is a schematic diagram showing the formation of a plume of plasma upon a target material receiving repeated pulses of a laser beam.

Further aspects and features of the example embodiments described herein will appear from the following description taken together with the accompanying drawings.

DESCRIPTION OF EXAMPLE EMBODIMENTS

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term, such as 1%, 2%, 5%, or 10%, for example, if this deviation does not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive-or. That is, "X and/or Y" is intended to mean X or X and Y, for example. As a further example, "X, Y, and/or Z" is intended to mean X or Y or Z or any combination thereof. Also, the expression of A, B and C means various combinations including A; B; C; A and B; A and C; B and C; or A, B and C.

The following description is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Recently, there has been a growing interest in developing new technologies of synthesizing isotopes from light elements and, more specifically, new technologies of synthesizing nanoparticles of stable isotopes from light elements, such as but not limited to Si, C, Zn, Ni or the like. In at least one embodiment, the apparatus, systems and methods described herein may be used to synthesizing nanoparticles of stable isotopes from elements having an atomic number less than about 80.

Typically, naturally occurring stable isotopes are a product of supernova explosions or neutron star mergers. Each of these processes offer extreme densities (e.g. greater than the density of a solid) and temperatures (e.g. $>10^4$ eV).

Ultrashort pulse lasers (i.e. lasers that emit pulses of light generally having a duration of the order of femtoseconds to ten picoseconds) having a peak power above one petawatt, for example, offer the potential to create high-energy-density plasmas (HEDPs) required to synthesize stable isotopes. For instance, others have created photonuclear reactions with a laser pulse having an intensity of $>10^{21}$ W/cm$^2$, corresponding to a peak power of ~one terawatt, interacting with a near-critical-density plasma.

However, herein methods and systems of synthesizing nanoparticles of stable isotopes using ultrashort laser ablation of a solid target material are disclosed.

Referring now to FIG. 1, a method 100 of synthesizing nanoparticles of isotopes according to at least one embodiment is shown therein. Method 100 includes at a first step 102 which involves converting a target material to a plasma state. Method 100 also includes at a second step 104 bombarding the target in the plasma state with the laser beam to maintain the target in the plasma state and synthesize the nanoparticles of an isotope of the target material.

In at least one embodiment, the methods and systems described herein utilize a laser having a pulse duration in a range of about 1 fs to about 300 ps.

In at least one embodiment, the methods and systems described herein utilize a laser beam pulse on a target material where the laser beam pulse has a much lower intensity than has previously been described for the creation of photonuclear reactions, such as being greater than about $10^8$ W/cm$^2$, or being about $10^{15}$ W/cm$^2$. The product of these photonuclear reactions are nanoparticles of the isotopes of the target material. The presence of the photonuclear reactions is initiated by ablating the target material (i.e. a solid) to convert the target material to a plasma state and, subsequently, bombarding the target material in the plasma with the laser beam.

At step 104, once the plasma has been generated at step 102, there is a threshold value of each of the pulse frequency of the laser beam and the peak laser intensity of the laser beam that is required to maintain the plasma for a duration that is sufficient for the synthesis of nanoparticles of an isotope of the target material. A schematic illustrating the formation of a plasma of a target material upon the target material receiving pulses of laser light is shown in FIG. 2.

Below the threshold value of the laser peak power (i.e. a laser peak power threshold), the target material will not be ablated and the plasma will not be enhanced and accelerated, irrespective of the pulse frequency of the laser beam. The laser peak power threshold is target material specific, and can be determined by experiments with all other parameters fixed. However, the laser peak power threshold does appear to be related to ionization energy since materials with higher ionization energy usually have higher laser peak power threshold.

It has also been determined that the threshold pulse repetition frequency may be kept above a threshold frequency value to inhibit the plasma from dissipating within a period of time between receiving pulses of the laser beam. A maximum time interval between subsequent pulses of laser beam may be based on the dynamics of the target material plasma. For instance, in at least one embodiment, the plasma is able to maintain a sufficiently high density and sufficiently high temperature for the synthesis of nanoparticles of an isotope of the target material when the time interval between pulses is in a time scale in the order of nanoseconds, which points to a pulse repetition frequency in the range of about 100 kilohertz (kHz) to about 100 megahertz (MHz).

In at least one embodiment, the threshold frequency value of the pulse repetition frequency is dependent upon parameters of the laser beam and/or an environment that the target material is in when it interacts with the laser beam. For instance, this may include but is not limited to a gas pressure of in a range of about 2 to about 6 barr, for example, in the environment around the target material and the rate of gas flow near, around or on the target material when it receives the laser beam.

In the apparatus, systems and methods described herein, in at least one embodiment, femtosecond laser ablation of a target material can be used to generate a high temperature plasma including particles of the target material. Herein, the term "high temperature plasma" refers to a plasma having a temperature in a range of about 3,000° C. to about 10,000° C. The high temperature plasma also includes ions and free electrons. When the femtosecond laser has an intensity of about $10^{15}$ W/cm$^2$, ablation of the target material is generally contributed by thermal vaporization, producing mostly neutral species.

In the apparatus, systems and methods described herein, a threshold peak power of about $10^{21}$ W/cm$^2$ on the surface of the target material generates a high-energy, high-density proton flux for an ultrashort duration, such as but not limited to a duration as short as about 10 ps. This laser intensity is above the critical power of laser self-focusing in a near-critical-density plasma. A high-energy electron beam (e.g. an electron beam with cutoff energy higher than about 100 MeV) can also be generated by interacting with a near-critical density plasma. Existing commercial ultrashort lasers typically provide maximum peak power in the order of $10^{15}$ W/cm$^2$ in a single laser pulse, which is generally not sufficient for generating the aforementioned high-energy, high-density proton flux or the aforementioned electron beam. However, if laser pulses interact with a hot plasma (e.g. plasma created with an ultrashort laser, for instance having a temperature up to about 10,000° C.), the threshold peak power of the laser can be significantly reduced. For instance, without limiting the foregoing, a laser with a pulse repetition rate (e.g. frequency) in a range of about 200 kHz to about 250 MHz provides for an interval between two consequent pulses of light from the laser beam being in the range of about one nanosecond. At this time scale, acceleration of electrons within the generated plasma is possible.

The plasma excitation temperature and the plasma electron density are generally highest at the first approximately 20 ns to approximately 100 ns after the laser interacts with the target material.

The plasma-ambient interaction occurs at about 100 ns after the laser beam interacts with the target material. Plume condensation and particle formation occurs at about 1 millisecond (ms) after the laser interacts with the target material. Upon condensation of the plume of the plasma, the plasma temperature and the plasma density reduces. The time scale shows that with laser pulses having a repetition rate in a range of about 200 kHz to about 250 MHz, the plasma will not cool down and the electron density will not reduce before the next pulse strikes the plasma. If the time interval between pulses is short enough, the temperature of the plasma is enhanced after multiple shots of laser pulses, such as but not limited to a number of shots in a range from about two shots to approximately a few thousand shots, and the plasma remains hot and dense (e.g. a near-critical density plasma) until the laser source is turned off. In this manner, the energy level of the electrons within the plasma may be enhanced after repeated laser irradiation of the plasma. Therefore, after a few pulses of repeated irradiation (e.g. in a range of about 10 pulses to about 1000 pulses), the electron energy of the plasma can reach a level high enough to induce a photonuclear reaction. Table 1 shows electron density values and plasma temperatures of plasmas for laser fusion and laser-produced plasmas.

TABLE 1

| Densities and temperatures of plasma generated by laser beam | | |
|---|---|---|
| Type | Electron density $N_e$ (cm$^{-3}$) | Temperature $T_e$ (eV$^a$) |
| Laser fusion | $10^{25}$ | $3 \times 10^3$ |
| Laser-produced | $10^{18} - 10^{24}$ | $10^2 - 10^3$ |

1 eV = 11600K

After the initial pulse irradiation, nanoparticles of an isotope are formed in the plasma. In at least one embodiment, the nanoparticles have an aerosol-like nanostructure. For example, in at least one embodiment, the length scale of these structures is generally not more than the laser wavelength. The presence of nanostructures in the plume further enhances laser irradiation of the plasma. Prior studies have shown that the characteristic expansion velocity of a plasma is about 100 nm/ps. Therefore, in about 1 ps, the plasma does not have enough time to fill the micrometric voids typical of low-density nanostructures. Thus, the formed nanostructures survive long enough in the plume to influence the interaction with the laser. The nanostructured plasma allows for a stronger laser energy absorption and a much higher conversion efficiency of laser energy into ion kinetic energy. Therefore, enhanced physical phenomena that would otherwise require higher laser intensities may occur at much a lower intensity.

High energy electrons present in the plasma can induce the photonuclear reactions in the plume introduced above. As a result, all types of isotopes can be generated.

The laser plume, both with or without interaction with subsequent laser irradiation, cools and condenses and, as a result, nanoparticles form. Rapid cooling and condensation occurs about 1 μs after the start of laser irradiation. At a pulse frequency in a range of about 200 kHz to about 250 MHz and a time interval between pulses of less than about 1 μs, there is a very short period of time for condensation before a next laser pulse irradiates the plume and heats it up again. Therefore, the particles will not grow much after nucleus formation. This influences both the particle size and structure. Accordingly, nanoparticles of very small size (e.g. sub-10 nm diameter) can be obtained. In some conditions, particles having a diameter of less than 1 nm may also be obtained.

Generally, the electron energy and plasma temperature are higher if the plume is at atmospheric pressure rather than in a vacuum. Therefore, in at least one embodiment, the presence of background gas can be adjusted to favor isotope formation. In at least one embodiment, a vacuum environment may be adopted such as but not limited to when isotopes of pure elements are desired. In at least one embodiment, the background gas may be reactive or non-reactive. For instance, in the presence of oxygen, oxidation will occur during the plume expansion. In this example, the synthesized nanoparticles can be a mixture of the target material and all types of oxides of the target material.

In at least one embodiment, when laser irradiation of the target material is conducted at atmospheric pressure, the product may be mixture of nanoparticles of the target material and oxides with a trace of nitrides of the target material (e.g. since oxygen ionization energy is lower than nitrogen). Oxygen typically reacts with target molecules first and dominates the chemical reaction, so there is less possibility of nitrogen reacting with the target material when the target material is in atmosphere.

In at least one embodiment, the addition of background gas helps to tune the crystalline structure of the nanoparticle. For instance, the density of lattice vacancy may be tuned to tailor the properties of the nanoparticle. Here, as described earlier, the species in the plasma first forms nuclei and grows in size due to collisions with other species in the plasma. At this time, the species in the plasma are in the liquid phase as droplets. These droplets tend to move outwardly from the plasma towards the interface of the plasma and the atmosphere due to dynamics of exploding plasma. As the droplets approach the interface, the temperature of the droplets decreases and the droplets may solidify, at which time the growth of the nanoparticle stops. All of the above happens in a short time window, such as but not limited to a time window of less than about 1 ms.

For crystallized materials, it takes time and energy to form a well-structured crystal. For instance, if the time of growth is too short, crystal formation may be incomplete and leave defects (e.g. vacant chemical bonds) in the crystal. Vacant chemical bonds increase the reactivity of the nanoparticles to other molecules and therefore may be preferred for some applications. The density of lattice vacancy refers to the amount of vacant chemical bonds in unit volume.

Further, in at least one embodiment, the pressure and the flow rate of the background gas may be used to control the size of the nanoparticles. For example, at a constant flow rate, increasing the pressure may lead to reducing the particle size of the nanoparticles. Further, in at least one embodiment, maintaining a constant pressure and increasing the flow rate of the background gas may lead to enriching certain types of nanoparticles.

In at least one embodiment, a plurality of nucleus reactions occur in the process of ultrashort laser synthesis of isotopes. As a result, all known isotopes can be found in the product.

In at least one embodiment, adjusting laser parameters may control the concentration/ratio of isotopes. For instance, as described above, laser processing parameters such as, but not limited to, laser wavelength, laser pulse duration, laser power, pulse frequency, for example, as well as type of background gas, pressure and/or flow rate of the background gas may be adjusted to enrich a selected type of isotope in desired particle size and lattice vacancy density.

In at least one embodiment, the methods and systems described herein synthesize stable isotopes in the form of nanoparticles. For instance, the nanoparticles of stable isotopes may have a particle size in a range of about 100 nm to about 2 nm.

In at least one embodiment, the combined effects of the type of isotope, the quantum-to-nano size of the particles and the size and/or number of vacancies can be controlled to provide unique properties that cannot be found in nanoparticles synthesized with other methods. In at least one embodiment, the size of the vacancies and/or the vacancy density can be controlled by changing the parameters of the laser and/or the gas. For instance, increasing the power of the laser and decreasing the frequency (e.g. to about 1 MHz) of the laser tends to form smaller particles with more vacancies. In at least one embodiment, supplying oxygen gas to the environment of the plasma tends to reduce the particle size and increase the vacancy density of the nanoparticles. For instance, in at least one embodiment, supplying oxygen gas to the environment of the plasma at a pressure of about 2 barr provides nanoparticles with a smaller particle size and denser vacancy than supplying oxygen gas to the environment of the plasma at a pressure of about 6 barr. Further, supplying nitrogen gas to the environment of the plasma increases particle size and reduces vacancy density.

In at least one embodiment, decreasing the wavelength of the laser tends to decrease the particle size of the nanoparticles generated therewith.

When a laser beam passes through a harmonic crystal, its wavelength generally reduces to one-half of its original wavelength. This can be referred to as generating a second harmonic, or frequency doubling. The fundamental beam and second harmonic beam can then generate a third harmonic beam in a process often referred as frequency tripling.

For example, for a fundamental wavelength of 1030 nm, the second harmonic is 515 nm and the third harmonic is 343 nm.

The output beam from harmonic crystals is a mix of the fundamental beam and frequency double/tripled beam. As noted above, decreasing the wavelength of the beam typically reduces the particle size of the nanoparticles generated. A mixed beam may also be used for material ablation.

In at least one embodiment, an ultrashort laser with specific parameters may be used to synthesize nanoparticles of stable isotopes. For instance, the ultrashort laser may have a pulse duration that is less than about 10 ps, a pulse frequency that is greater than about 200 KHz and an average power that is greater than about 10 watts.

In at least one embodiment, the methods and systems described herein synthesize stable isotopes in the form of nanoparticles (e.g. particles having a diameter less than about 100 nm).

In at least one embodiment, the laser wavelength can range from 1100 nm to 250 nm (e.g. from the UV to the IR range) for both the fundamental and associated harmonics, i.e. the $1^{st}$ and second harmonic frequencies.

In at least one embodiment, the focused laser spot size can range from about 2000 micrometer (μm) to about the wavelength of the laser. In some embodiments, the spot size is preferably about 10 μm. The peak laser intensity can then be determined by: peak laser intensity=pulse energy/pulse duration/laser spot area. The pulse energy of each laser pulse is determined by: pulse energy=laser average power/pulse frequency.

In at least one embodiment, the target material can be any solid, including but not limited to a metal, a non-metal, a semiconductor and/or a compound. For example, in at least one embodiment, the target material can be a commonly used metal such as but not limited to iron, nickel, aluminum, titanium, copper, zinc, gold, silver, platinum, and their alloys and compounds. As another example, in at least one embodiment, the target material can be a semiconductor such as but not limited to silicon, germanium, gallium arsenide, and compounds thereof. As yet another example, in at least one embodiment, the target material can be a special alloy such as but not limited to an Al—Si alloy and/or a Ti—Al alloy. In at last one embodiment, the target material can be carbon, graphite, and/or a graphite intercalation compound.

The various parameters of the laser that is used to create the stable nanoparticle isotopes (also referred to herein as nano-isotopes) in accordance with the teachings herein are interrelated and may be varied at the same time to use values that are suitable for the particular application or at hand or hardware that is used in synthesis.

For instance, if the peak laser intensity is high such as above about $10^{15}$ W/cm$^2$, for example, then the frequency of the laser pulses may be reduced to about 200 kHz. Alternatively, if the peak laser intensity is low, such as lower than about $10^{14}$ W/cm$^2$, then the pulse frequency has to be increased, say above about 1 MHz, in order to maintain the plasma state for the target material. In other words, the combination of the pulse frequency and the peak laser intensity can be selected so that: (1) the plume does not dissipate before the next laser pulse irradiates the target material; and (2) the next pulse has enough energy to accelerate the species in the plume. However, the peak laser intensity is also determined by the pulse frequency. Both parameters have a threshold value in order to keep the plasma active.

For example, one set of parameters that may be used include a laser spot size of about 10 μm, a laser pulse repetition frequency of about 1-25 MHz, a laser average power of about 15 watts, a pulse duration in the range of about 200 fs to about 10 ps. The combination of these parameters provides a peak laser intensity of about $10^{14}$ to $10^{15}$ W/cm$^2$. These parameters were found to result in the production of isotope nanoparticles from various types of solid target materials and the isotope yield is an increase of a few percent compared to the same isotopes that are naturally occurring. However, with higher average laser power (about 100 W at about a 50 fs pulse duration), the yield of isotope nanoparticles may increase several times. An empirical relationship may be used to show the relationship of between nano-isotope yield and peak laser intensity for a certain material.

Apparatuses

The nanoparticles of stable isotopes synthesized using the methods described herein can be synthesized in different forms and/or using different apparatuses and/or systems. At least three different possible configurations for apparatuses and/or systems for synthesizing the nanoparticles of stable isotopes are described herein as examples.

Generally, the apparatuses nanoparticles of an isotope from a target using a laser beam include a laser that is configured to generate laser beam pulses and an optical arrangement that is optically coupled to the laser source and configured to receive the laser beam pulses and direct the laser beam pulses towards the target.

In at least one embodiment, the laser may have a built-in pulse-frequency and power controller. In some cases, the power can be tuned continuously and the pulse-frequency can be selected from several preset values.

In at least one embodiment, the optical arrangement includes one or more optical components (e.g. beam expanders, harmonic generators, convex lenses, concave lenses, scanning lenses, waveplates and/or galvo scanners and/or the like) typically known by those skilled in the art. The optical components are arranged to receive the laser beam pulses from the laser and direct the laser beam pulses towards the target.

Figure 3:
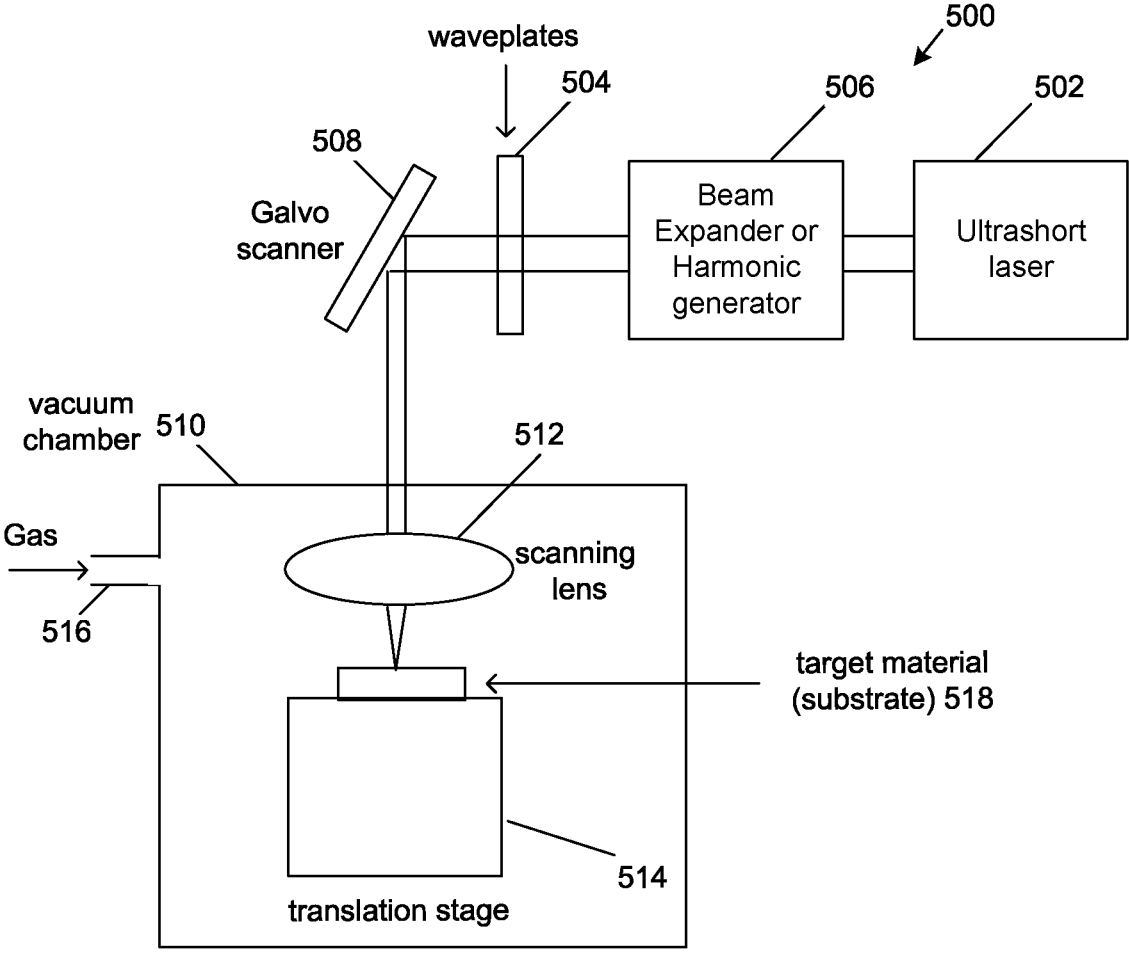
FIG. 3 is a schematic diagram showing an example embodiment of a device for synthesizing nanoparticles of an isotope, according to the teachings herein.

Referring to FIG. 3, an example embodiment of a system 500 that can be referred to as a laser direct writing system, may be configured to create isotope nanoparticles from a target material and deposit the isotope nanoparticles on a substrate. System 500 includes an ultrashort laser 502 that directs laser light through a beam expander or harmonic generator 504. Laser light exits the beam expander or harmonic generator 504 and passes through one or more waveplates 506 and then a galvo scanner 508 redirects the laser lights towards a vacuum chamber 510. A background gas is injected into the vacuum chamber 510 at an inlet 516. As the laser light enters the chamber 510 it is focused by a scanning lens 512 onto a surface of a target material 518 supported on a translation stage 514. The translation stage 514, which can be an electro-mechanical arrangement as known by those skilled in the art, can be used to move the target in the x-y axis, for example to create some type of geometric pattern.

During operation, the system 500 is used to deposit nano-isotopes directly onto a microdevice, including but not limited to integrated circuits, micromechanical microengineering systems (MEMS) and microchips. Galvo scanner 508 is used to move the laser spot on the substrate surface with high positioning accuracy to create a desired geometric pattern. The scanning lens 512 is used to focus the moving laser spot on to the substrate surface without optical distortion. The operation of the system 500 is similar to a laser direct writing system, commonly used in the semiconductor industry.

In at least one embodiment, the configuration of system 500 can be integrated into a standard micromechanical microengineering system (MEMS) fabrication process so that the isotope nanoparticles can be integrated into a microdevice (not shown). For instance, the microdevice may be a MEMS microchip, or an integrated circuit (IC) and the isotope nanoparticles may be used in sensors thereon.

Figure 4:
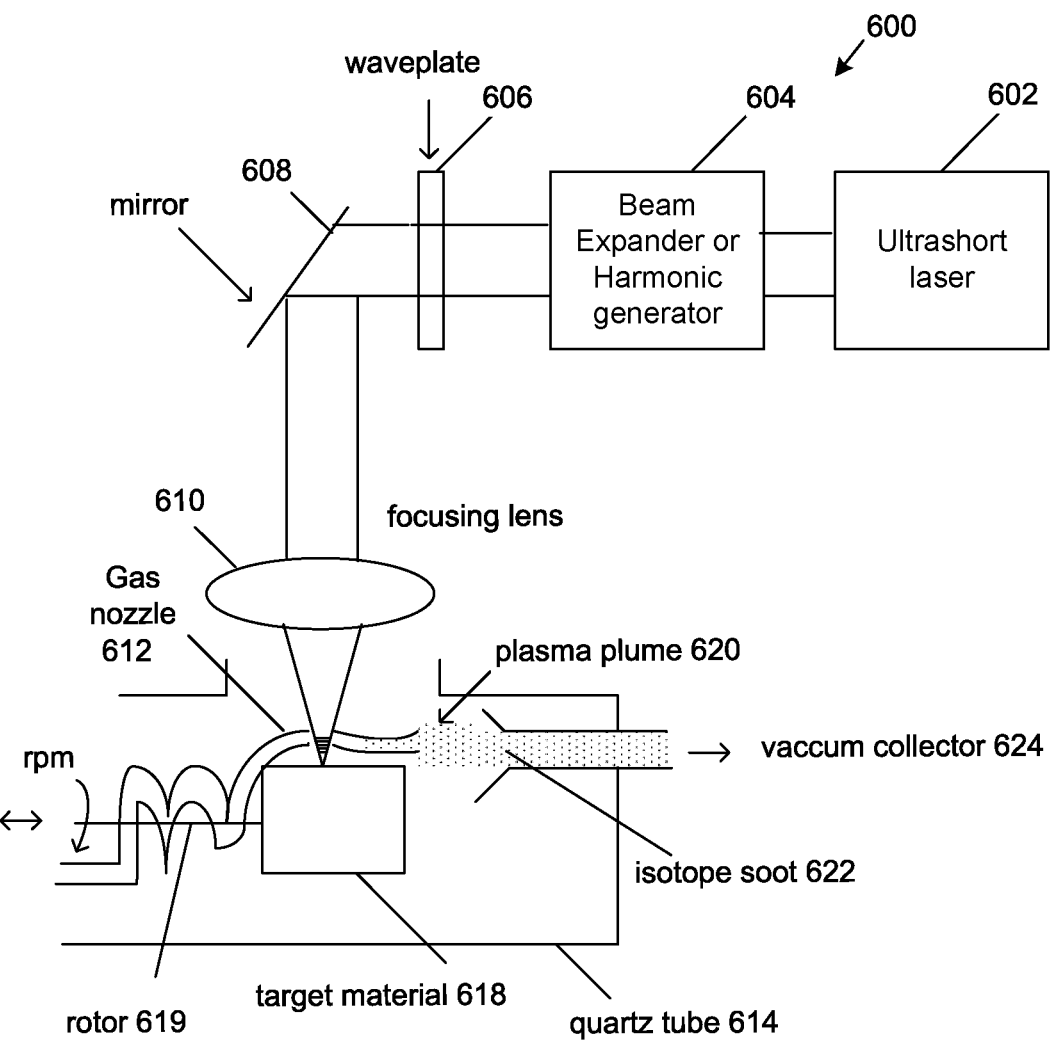
FIG. 4 is a schematic diagram showing another example embodiment of a device for synthesizing nanoparticles of an isotope, according to the teachings herein.

As shown in FIG. 4, system 600 is another example embodiment of a system for synthesizing nanoparticles of isotopes in accordance with the teachings herein. System 600 may be referred to as a system performing free-particle nano-isotope synthesis for synthesizing free-particles (e.g. soot) of nano-isotopes. The collected soot can then be processed into different forms, dependent on the end user's needs. For example, the collected soot can be cemented into disks and/or cubes or can be suspended in a solution.

System 600 includes an ultrashort laser 602 that generates laser light which is then, optionally directed through a beam expander or a harmonic generator 604. Laser light exits the beam expander or harmonic generator 604 and optionally passes through one or more waveplates 606 and then a mirror 608 redirects the laser light towards a focusing lens 610 that focuses the laser light onto a target material 618 housed in a tube 614. In at least one embodiment, the tube 614 can be a quartz tube. Quartz can withstand high heat and is transparent, so can provide for viewing or monitoring the sample (i.e. the target material 618). In at least one embodiment, the tube 614 may also be a ceramic tube.

In at least one embodiment, the beam expander or harmonic generator 604 is implemented right after the laser system before entering into beam expander 604 or the one or more waveplates 606. Waveplate(s) 606 can be placed before or after or in the middle of beam expander 604, depending on the available space and convince of installation/adjustment. In at least one embodiment, waveplate 606 may be placed in the middle of beam expander 604 with a convergent incoming laser beam, if radial polarization is desired.

It should be understood that the optics described herein, such as but not limited to the beam expander or a harmonic generator 604 and/or the waveplate(s) 606, should be made with materials that are able to withstand the high powers of laser pulses described herein (e.g. materials that do not breakdown under laser irradiation).

In at least one embodiment, the laser light ablates a surface of the target material 618 as a tube that is coupled to a gas nozzle 612 directs a gas (e.g. a reactive gas such as but not limited to oxygen or a non-reactive gas such as but not limited to argon) towards the surface of the target material 618 which forms a plasma plume 620 and isotope soot 622. The isotope soot 622 is collected by a vacuum collector 624. In at least one embodiment, the system 600 includes a rotor 619 configured to rotate the target material 618 as it is being ablated. The rotor 619 turns, for example, at a speed in a range of about 1,000 to about 10,000 rpm. In at least one embodiment, speeds less than about 1,000 rpm may also be possible. The speed of the rotor 619 is typically dependent on the ablation threshold of the target material 618. For example, if the target material 618 is hard to ablate, the rotor 619 may rotate at a slower speed.

During operation, the system 600 is used to generate loose nano-isotopes. In system 600, the tightly focused laser spot ablates the target material 618. Target material 618 is rotated by rotor 619 at high speeds in a range of about 1,000 to 10,000 rpm. The rotation spins the formed nano-isotopes out of the plasma and allows for continuous feed of fresh unablated target material 618. Gas flows out of the nozzle 612 blows the free-flying nano-isotopes toward vacuum collector 624, where the loose nano-isotopes are collected in the form of soot 622. Higher rotation speeds of rotor 619 will generate higher yield of nano-isotopes with the compromise of the concentration of desired isotope type. Reactive or nonreactive gas can be supplied. The gas temperature can be adjusted depended on the production need. Lower temperature increases the vacancy density, while preheating may increase the production yield and isotope conversion. The adjustment of laser parameters is the same as described elsewhere herein.

Figure 5:
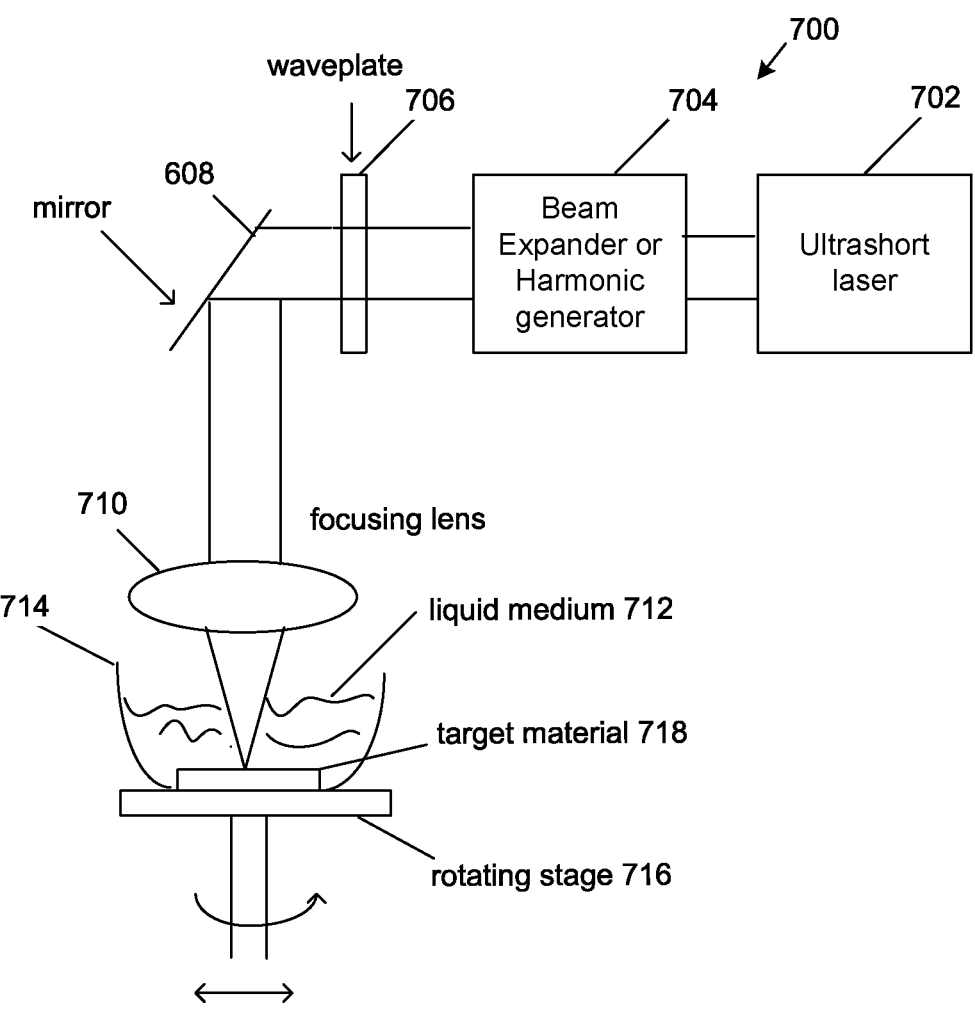
FIG. 5 is a schematic diagram showing another example embodiment of a device for synthesizing nanoparticles of an isotope, according to the teachings herein.

As shown in FIG. 5, system 700 is another example embodiment of a system for synthesizing nanoparticles of stable isotopes in accordance with the teachings described herein. System 700 synthesizes loose particles, i.e. nanoparticles, of stable isotopes suspended in a liquid medium. The system 700 may be referred to as a free-particle nano-isotope synthesizer.

System 700 includes an ultrashort laser 702 that directs laser light through a beam expander or harmonic generator 704. The laser light exits the beam expander or harmonic generator 704 and passes through one or more waveplates 706 and then a mirror 708 which redirects the laser lights towards a focusing lens 710 that focuses the laser light onto a target material 718 immersed in a vessel 712 filled with a liquid medium 712. The vessel 714 sits on a rotating stage 716 that is configured to rotate the target material (see above). Here, the top surface of the target material 718 is typically stripped off and converted into soot. Rotation of the target material 718 may provide a supply of fresh target material 718.

In at least one embodiment, vessel 714 may be a glass or a ceramic tank.

In at least one embodiment, the target material 718 may be placed in a variety of liquid media 712, such as but not limited to solvents such as but not limited to distilled water, alcohol and/or an aqueous solution of polyvinylpyrrolidone.

Ablation in liquid, for instance as is shown in FIG. 5, may offer many features such as but not limited to smaller particle sizes of isotopes relative to other methods of ablation, pure chemical composition of the isotope nanoparticles (because oxidation is avoided.) and/or the attachment of organic groups on the surface of the isotope nanoparticles. Organic groups added to the isotope nanoparticles may add many biofunctions to the isotope nanoparticles.

During operation, the system 700 is used to create nano-isotopes in liquid. The vessel 714 is filled with liquid 712, such as distilled water, alcohol and organic solvent. The temperature of the liquid 712 may be controlled to tune the properties of the nano-isotope. Cooled liquid or preheated liquid may be used. In some cases, liquid 712 may react with the target material 718 under laser irradiation and form a nano-isotope compound. In some cases, liquid 712 may not react with target material 718 and simply provide a medium for synthesis. Ultrashort laser 702 is focused under the liquid 712 surface onto the top surface of the solid target 718. In at least one embodiment, a table, for example, that holds the vessel 714 may rotate at low speed to provide continuous supply of fresh target surface of target material 718. The produced nano-isotopes may be collected, dried, and processed into desired forms.

Figure 6A:
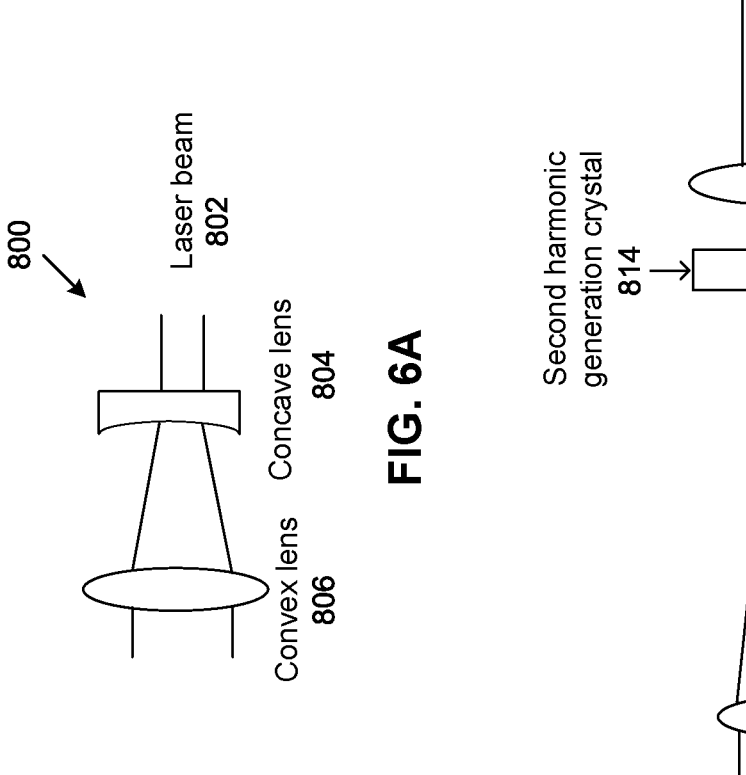
FIG. 6A is a schematic diagram showing light passing through a beam expander having a convex and concave lens, according to at least one embodiment.
Figure 6B:
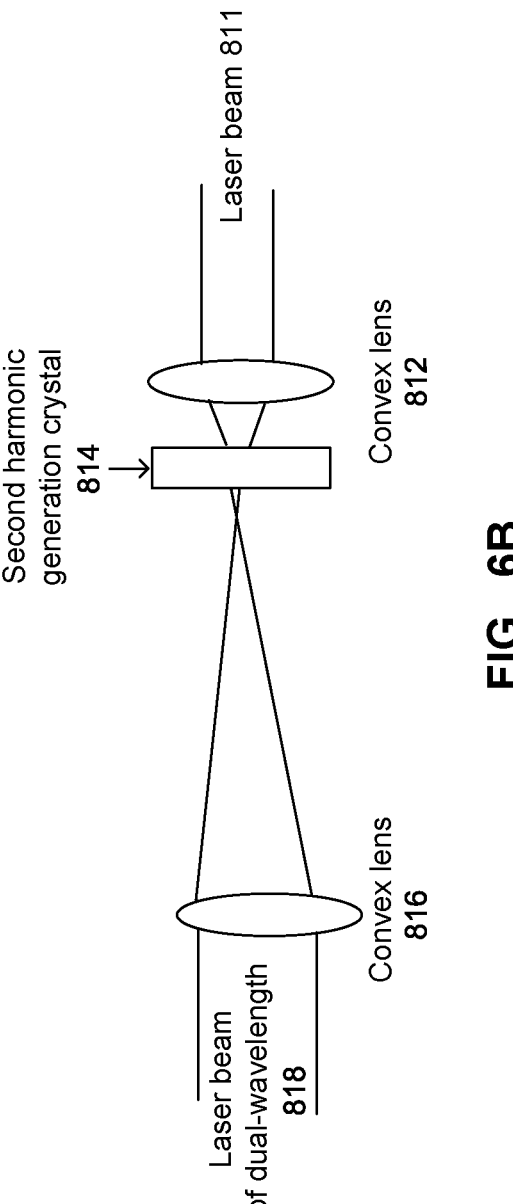
FIG. 6B is a schematic diagram showing light passing through a second harmonic generator, according to at least one embodiment.

FIGS. 6A and 6B show examples of a common beam expander 800 (FIG. 6A) and a common harmonic generator 810 (FIG. 6B) for use as described above. FIG. 6A shows that the width W of a laser beam 802 can be expanded by passing the beam through a concave lens 804 and a convex lens 806.

FIG. 6B shows a common harmonic generator 810 including a first convex lens 812, a second harmonic generation crystal 814, a second convex lens 816. Laser beam 811 passes through the first convex lens 812 and the second harmonic generation crystal 814 and the second convex lens 816 to form a laser beam of dual wavelength 818.

Example Applications

The nanoparticles of isotopes that can be synthesized by the methods and the systems described herein demonstrate unique physical, optical and biological properties that appear not to have been observed from nanoparticles synthesized by other means. For instance, with respect to unique physical properties, the generation of nanoparticles with sub-1 nm size have been demonstrated. Further, the crystalline nanoparticles having a very dense vacancy have been demonstrated. These nanoparticles may have ultra-sensitivity and therefore be useful, for example, in molecular detection.

For instance, with respect to unique optical properties, the nanoparticles formed using the apparatus, systems and methods described herein typically have brighter fluorescence and are very stable, with little photo bleach, for about 48 hours.

With respect to unique biological properties, the nanoparticles formed using the apparatus, systems and methods described herein are generally biocompatible, biodegradable and able to, for example, selectively target cancerous cells.

These unique properties may find many applications in different fields of endeavor, including but not limited to the applications provided below.

Figure 7:
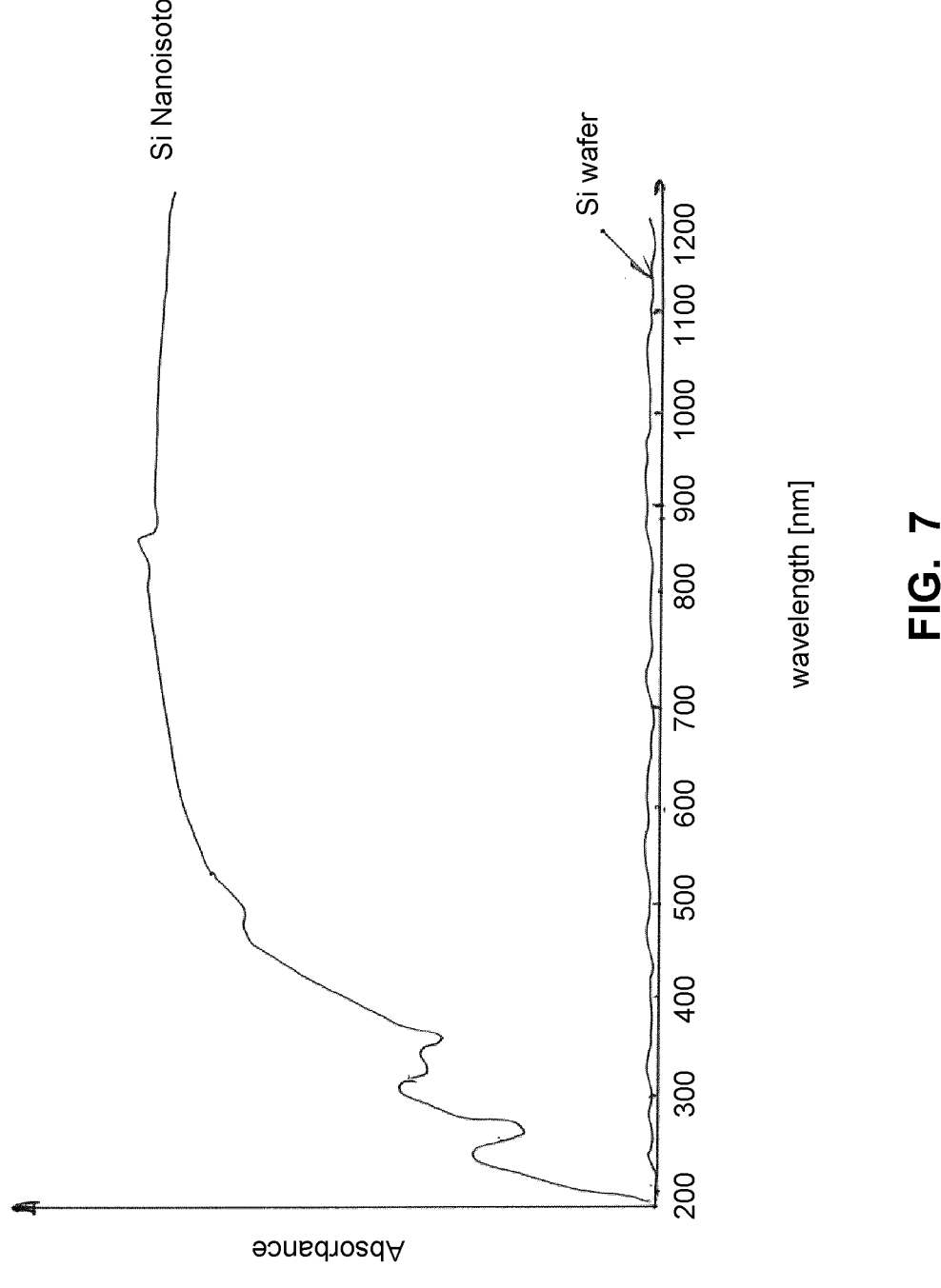
FIG. 7 is a graph showing how isotope nanoparticles absorb light having wavelengths in the ultraviolet (UV) to infrared (IR) spectrum, harvesting more photons over a wider range of the solar spectrum.

In a first example application, the nanoparticles of stable isotopes (referred to hereafter as stable nano-isotopes) synthesized by the apparatus, systems and methods described herein may be used for full spectrum solar energy absorption. Referring to FIG. 7, the graph therein shows that nano-isotopes of Si absorb light having a wavelength in the ultraviolet (UV) to infrared (IR) range, harvesting more photons over a wider range of the solar spectrum. Potential applications of the nanoparticles of stable isotopes, including but not limited to Si isotopes and $TiO_2$ isotopes, synthesized by the apparatus, systems and methods described herein used in full spectrum solar energy absorption may include high-efficiency solar cells, high-sensitivity photon detectors and high-efficiency photo catalysis, among others.

In another example application, the nanoparticles of stable isotopes synthesized by the apparatus, systems and methods described herein may also be used for surface enhanced Raman scattering for biomolecule detection. Here, nanoparticles of materials such as but not limited to gold, silver, platinum, titanium, silicon, aluminum, nickel, and/or graphite may be used for surface enhanced Raman scattering for biomolecule detection. This is because nano-isotopes that are synthesized in accordance with the teachings herein present unique properties that may provide advantages in bio-detection. These properties may include, but are not limited to, cleanliness, higher detection sensitivity, chemical stability, less toxic and easier to use, for example.

With respect to cleanliness, the quantum dots (i.e. nano-isotopes with particle size less than about 5 nm) formed using the nano-isotopes synthesized by the methods and systems described herein may be free of chemicals. Unlike all other types quantum dots, the quantum dots produced using the nanoparticles synthesized using the methods and systems described herein are generally non-toxic, making them particularly suitable for biomedical application. In addition, the dots are free of contaminations and generally do not react/interfere with target molecules. Laser synthesis is a physical-chemical process and does not involve toxic chemicals, so is free of chemical residues. In contrast, commonly used nanoparticles are the product of a chemical reaction. Residue chemicals are unavoidable despite use of a cleaning process. A biocompatible agent is required to coat the surface of the particles to suppress the toxicity.

Nanoisotopes described herein may have a retention time in cells in a range of about one hour to about 2 two months. The retention time of the nanoparticles may be tuned depending on the application. For instance, the retention time of the nanoparticles may be configured to be in a range of about one hour to about six hours for diagnostic applications and may be configured to be in a range of about one day to about seven days, or longer, for therapy applications.

With respect to higher detection sensitivity, the quantum dots formed using the nano-isotopes synthesized by the methods and systems described herein are smaller and have a unique structure (e.g. have a high vacancy density of crystalline nanoparticles) compared to current quantum dots, which translates to higher detection sensitivity, which translates to higher detection sensitivity, and pushes the limit of detection to a lower concentration. Therefore, previously undetectable traces (undetectable because of their low concentration) may be detected using quantum dots formed using the nano-isotopes synthesized by the methods and systems described herein. It should be noted that a limit of detection (LOD) is the lowest concentration that can be sensed by a sensor and, with higher sensitivity, the LOD may be lowered.

With respect to suitability, conventional commercial quantum dots are mostly made from gold and silver. Although semiconductor and other non-metallics are more preferable for biomedical applications, these materials do not find real-world application due to unsatisfactory performance due to low sensitivity of semiconductor quantum dots. However, the nano-isotopes synthesized by the methods and systems described herein can be used to produce quantum dots from a wide range of materials, including metals, semiconductors and carbon. The performance of these non-metallic quantum dots is comparable to the quantum dots made from gold and silver because, for example, of the high density of the vacancies in the lattice. Table 2 shows the limits of detection and enhancement factors of some nano-isotopes.

TABLE 2

| Limits of Detection and Enhancement Factors for Nano-isotopes | | |
|---|---|---|
| Nano-isotopes | Limit of Detection (Molar) | Enhancement Factor |
| $TiO_x$ | $10^{-9}$ | $\sim 10^{10}$ |
| Si | $10^{-9}$ | $\sim 10^{13}$ |
| C | $10^{-15}$ | $\sim 10^{14}$ |
| Ni | $10^{-15}$ | $\sim 10^{14}$ |

Note: Commonly used gold nanoparticles have a typical limit of detection around $10^{-9}$ molar and an enhancement factor in the range of about $10^{10}$-$10^{15}$.

In another example application, Si nano-isotopes synthesized by the apparatus, systems and methods described herein may also be used for virus/bacterial infection diagnosis. Rapid diagnosis of viral infection is critical for the prevention of virus spreading. Surface enhanced Raman spectroscopy (SERS) is the most promising technique for rapid diagnosis of virus/bacterial infection. SERS detects biomolecules finger-prints of virus/bacterial, including surface proteins, genetic materials or antibody, in under a minute. Biomolecules finger-prints are virus/bacterial type specific. The analysis of SERS information will allow for the diagnosis of virus/bacterial infection, as well as other types of disease. The stable nano-isotopes may be used a probe of the SERS. Because of the high sensitive of nano-isotopes, the virus/bacteria may be detected from patient samples that usually has a lower concentration of virus/bacteria, such as saliva. Because saliva is much easy to collect compared to biopsy from other body locations, this technique will enable massive screening of the general public. In addition, SERS will allow the detection of multiple makers of virus/bacterial simultaneously, therefore, better accuracy of diagnosis can be expected.

In another example application, Si and graphite nano-isotopes, and alternatively metal or noble metals, synthesized by the apparatus, systems and methods described herein may also be used for cancer pathological analysis. Current pathological diagnosis is mostly based on microscopic images. This involves processing biopsied materials so that they are placed onto slides. Microscopic images of the slides are then obtained. The microscopic images of the slides are then reviewed by a trained medical doctor. Cell shape and other visual characteristics are used to manually identify if there is cancer in the biopsy sample and the type of cancer. The size of cancer cell can be measured but other characteristics, such as metastasis, cannot be determined. The accuracy of current diagnosis method depends on imaging equipment and the type of biopsy. More importantly, minute cancer tissues at the early stage of development cannot be captured due to magnification power of the equipment. For instance, SERS can be used. SERS is a diagnosis method based on the detection of biomolecules. Therefore, SERS is much more sensitive and accurate than image-based diagnosis. SERS, for example, may sense the biomolecule finger-prints of cancerous tissue before a patient starts showing symptoms or before the tumor is visible under microscope, thus allow for early diagnosis.

In another example application, Si and graphite nano-isotopes, and alternatively metal or noble metals, synthesized by the apparatus, systems and methods described herein may also be used to analyze cancer tissue cells at the molecular level. Within 6-12 hours of cell culture, the quantum dots from stable nano-isotopes may dissipate all the way into a cell nucleus. Surface markers, RNA and DNA of cancer may then be revealed all at once. This is possible because each molecule occupies specific locations on the Raman spectrum (just like the X-ray spectrum). Different types of molecules, proteins, DNA/RNA, etc. each has a specific band. Simultaneous detection of different types of markers is then feasible. Therefore, cancer type and metastasis stage may be diagnosed with multiple indicators.

In another example application, Si and graphite nano-isotopes, and alternatively metal or noble metals, synthesized by the apparatus, systems and methods described herein may also be used for universal cancer screening and early diagnosis using liquid biopsy. Diagnosis with liquid biopsy, including bloody, saliva, urine, offers many advantages, including non-invasive, ease of collection and less pain to patient. For instance, samples collected for cancer blood tests are typically analyzed in a lab for signs of cancer.

The samples may show cancer cells, proteins or other substances made by the cancer. Commonly used blood tests include complete blood cell count, blood protein test and tumor marker test. Blood test results are not used alone for the diagnosis of cancer because several factors can influence test outcomes. Circulating cancer tumor cells (CTC) and circulating cancer stem cells (cCSCs) have been proposed as new markers for tumor diagnosis and therapy monitoring.

The circulating tumor cell test has emerged recently but isn't commonly used in a clinical setting. It is used only as an adjunct to standard methods of monitoring of patients with metastatic cancer. In short, information provided by current blood tests is very limited. They are only used as secondary diagnosis method in assistant to standard methods.

Circulating tumor cell (CTC) tests are described as cells shed by a primary tumor into vasculature and they keep circulating in the blood stream of cancer patients. CTCs are known to be circulating in the body fluids before they metastasize to various parts of the body even in primary stages of the disease. However, they are not easily identified, as they are present in a very small number. It is estimated that a teaspoon of blood might contain just about 5-50 CTCs.

cCSCs are a subset of CTCs and therefore their population is even scarcer. Similar to CTCs, cCSCs carries finger print information of cancer tumor and may be used a marker for cancer diagnosis.

As described above, the concentration of biomarkers (proteins, CTCs, cCSCs) in liquid biopsy is usually much lower than that in a tissue biopsy. Thus, liquid biopsy suffers poor diagnosis accuracy with current clinical test methods. The functionalized nano-isotopes may potentially lower the limit of detection and make liquid biopsy a reliable primary sample for medical diagnosis. Moreover, Raman analyzer has the ability to probe multiplex biomarkers simultaneously; therefore, improving diagnosis accuracy significantly. However, the sensitivity and applicability of CTC/cCSC-based cancer analysis is highly limited due to their scarcity. CTC test emerged recently but isn't commonly used in a clinical setting. It requires cell isolation and is used only as an adjunct to standard methods because of limited accuracy. Nano-isotopes detects both types of cells simultaneously, using multiplex analysis of biomarkers and DNA fingerprints. This holistic approach is expected to be more accurate and reliable than the existing method, which analyzes CTC surface markers alone. In addition, nano-isotopes analysis uses whole blood sample, thus further improves diagnosis accuracy by retaining the quantity of CTC/cCSC. The use of SERS with nano-isotopes as probes, will result in a cancer screening test that requires simpler operation and offers better diagnosis accuracy.

In another example application, the stable nano-isotopes synthesized by the apparatus, systems and methods described herein may also be used for single cell detection. Adding labels to quantum dots may provide specificity and allow them to attach only to CTCs. The high detection sensitivity of these labeled quantum dots may also allow for the detection of CTC from whole blood.

In another example application, the stable nano-isotopes synthesized by the apparatus, systems and methods described herein may also be used in trace material (e.g. drugs and explosives) detection, improved security and law enforcement, environment Pollutant monitoring, monitoring water for safe drinking, and fluorescence-based imaging, among other applications.

In another example application, metals, alloys, noble metals, graphite and silicon, semiconductors like $TiO_2$ nanoisotopes synthesized by the apparatus, systems and methods described herein may demonstrate superior performance compared to other fluorescent agents in biomedical applications and may be used to improve the current florescence-imaging methods for cancer and other image based diagnosis. Lab observation shows high brightness of these isotopes compared to other nanoparticles.

In addition, cancer cells tend to uptake nano-isotopes at a much higher rate. For instance, cancer cells are more than ten times more likely to uptake nano-isotopes than healthy tissue cells. The high dosage in cancer cells also makes them much brighter than healthy cells. The contrast makes cancer cells stands out.

Further, different types of cancer cell appear to have different tastes with respect to nano-isotopes (e.g. prefer certain materials, shapes and sizes of the nano-isotopes).

In another example application, graphite nano-isotopes synthesized by the apparatus, systems and methods described herein may also be used for cancer immuno-therapy. Immune cells like T-cells and/or natural killer (NK) cells have the ability to identify and target at infected host cells. T cells also called T lymphocytes are one of the major components of the adaptive immune system. NK Cells are lymphocytes in the same family as T cell. They may be used as a carrier to deliver the nano-isotopes to cancer niche. Once uptake by cancerous cells occurs, the nano-isotope may induce reprograming of the cancer cells or cancer stem cell, converting them to harmless tissues. This approach may be developed into medicines for personalized targeted cancer therapies. This approach can also be used for cancer diagnosis by combining SERS and Florescence based detection.

In another example application, the stable isotopes synthesized by the apparatus, systems and methods described herein may be used to differentiate between Amyloid species in Alzheimer's disease studies. For example, nanoparticle isotopes may be used for the measurement of in vivo protein translation in cells or deposition into plaques in normal or diseased brain to differentiate between Amyloid species.

In another example application, nanoparticle isotopes synthesized by the apparatus, systems and methods described herein may be used in energy harvesting applications. For example, the nanoparticle isotopes may be incorporated in materials that have a photovoltaic effect and may be used in solar cells to convert sunlight directly into electricity.

In another example application, nanoparticle isotopes synthesized by the apparatus, systems and methods described herein may be used in environmental pollutant detection applications. For example, the nanoparticle isotopes may be included in gas sensors or as an adsorbent to remove various types of organic and inorganic pollutants, both in air streams and in an aqueous environment.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

What is claimed is:

1. A method of synthesizing nanoparticles of an isotope from a target using a laser beam, the method comprising:
   generating the laser beam;

directing the laser beam to the target to convert the target into a plasma state; and bombarding the target in the plasma state with the laser beam to maintain the target in the plasma state and synthesize the nanoparticles of the isotope;

wherein, during bombarding the target in the plasma state with the laser beam, the laser beam is configured to have a pulse frequency and a peak laser intensity that accelerates electrons in the plasma state and maintains the plasma state at a temperature high enough to provide for the synthesis of the nanoparticles of the isotope.

2. The method of claim 1, wherein, during bombarding the target in the plasma state, the laser beam has a laser pulse width duration in a range of about 1 femtosecond (fs) to about 300 picoseconds (ps).

3. The method of claim 1, wherein, during bombarding the target in the plasma state, the laser beam has an average laser power that is greater than about 8 watts.

4. The method of claim 1, wherein, during bombarding the target in the plasma state, the laser has a pulse frequency in a range of about 200 kHz to about 250 MHz.

5. The method of claim 1, wherein, during bombarding the target in the plasma state, the laser has a laser wavelength in a range of about 250 nm to about 1150 nm at fundamental or higher harmonic frequency.

6. The method of claim 1, wherein, during bombarding the target in the plasma state, the laser has a focused laser spot size in a range of about 10 nm to about 2000 μm.

7. The method of claim 1, wherein, during bombarding the target in the plasma state, the laser has a peak laser intensity that is greater than about $10^8$ W/cm$^2$.

8. The method of claim 1, wherein, during the bombarding the target in the plasma state, the laser has a peak laser intensity greater than about $10^{15}$ W/cm$^2$ and a pulse frequency of about 200 KHz.

9. The method of claim 1, wherein the synthesized nanoparticles of the isotope have a stable state or a half-life time greater than about 20 minutes.

10. A method of generating high fluorescence excitation signals, the method comprising:

synthesizing nanoparticles of an isotope from a target using a laser beam, the synthesizing comprising:

generating the laser beam;

directing the laser beam to the target to convert the target into a plasma state; and bombarding the target in the plasma state with the laser beam to maintain the target in the plasma state and synthesize the nanoparticles of the isotope;

wherein, during bombarding the target in the plasma state with the laser beam, the laser beam is configured to have a pulse frequency and a peak laser intensity that accelerates electrons in the plasma state and maintains the plasma state at a temperature high enough to provide for the synthesis of the nanoparticles of the isotope; and using the nanoparticles of the isotope to generate high fluorescence excitation signals in biological diagnostic applications.

11. A method generating high surface enhanced Raman excitation signals, the method comprising:

synthesizing nanoparticles of an isotope from a target using a laser beam, the synthesizing comprising:

generating the laser beam;

directing the laser beam to the target to convert the target into a plasma state; and bombarding the target in the plasma state with the laser beam to maintain the target in the plasma state and synthesize the nanoparticles of the isotope;

wherein, during bombarding the target in the plasma state with the laser beam, the laser beam is configured to have a pulse frequency and a peak laser intensity that accelerates electrons in the plasma state and maintains the plasma state at a temperature high enough to provide for the synthesis of the nanoparticles of the isotope; and using the nanoparticles of the isotope to generate high surface enhanced Raman excitation signals in biological diagnostic applications.

12. A method of using nanoparticles of an isotopes in biomedical applications, the method comprising:

synthesizing the nanoparticles of the isotope from a target using a laser beam, the synthesizing comprising:

generating the laser beam;

directing the laser beam to the target to convert the target into a plasma state; and bombarding the target in the plasma state with the laser beam to maintain the target in the plasma state and synthesize the nanoparticles of the isotope;

wherein, during bombarding the target in the plasma state with the laser beam, the laser beam is configured to have a pulse frequency and a peak laser intensity that accelerates electrons in the plasma state and maintains the plasma state at a temperature high enough to provide for the synthesis of the nanoparticles of the isotope; and using the nanoparticles of the isotope in biomedical applications, the nanoparticles of the isotope having a biodegradable property.

13. An apparatus for synthesizing nanoparticles of an isotope from a target using a laser beam, the apparatus comprising:

a laser that is configured to generate laser beam pulses; and an optical arrangement that is optically coupled to the laser source and configured to receive the laser beam pulses and direct the laser beam pulses towards the target;

wherein the laser beam pulses are generated at a pulse frequency and a peak laser intensity to convert the target into a plasma state, maintain the target in the plasma state at a temperature high enough to synthesize the nanoparticles of the isotope.

14. The apparatus of claim 13 further comprising a vacuum chamber housing the target, the vacuum chamber having an inlet for receiving a background gas and directing the background gas towards the target while the target is ablated by the laser beam pulses.

15. The apparatus of claim 14 further comprising a vacuum collector configured to collect the isotope soot.

16. The apparatus of claim 13 further comprising a tube housing the target, the tube having an inlet for receiving a gas and directing the gas towards the target while the target is ablated by the laser beam pulses to generate a plasma plume and an isotope soot.

17. The apparatus of claim 16 further comprising a rotor configured to rotate the target within the tube as the target is ablated by the laser beam pulses.

18. The apparatus of claim 13 further comprising a vessel housing the target, the vessel being filled with a liquid medium and the target being positioned within the vessel below a surface of the liquid medium.

19. The apparatus of claim 18, wherein the liquid medium is a solvent.

20. The apparatus of claim 19, wherein the solvent is one of distilled water, alcohol and an aqueous solution of poly-vinylpyrrolidone.

* * * * *